United States Patent
Roy et al.

(10) Patent No.: US 8,538,701 B2
(45) Date of Patent: Sep. 17, 2013

(54) FLUID CONDUCTIVITY MEASUREMENT TOOL AND METHODS

(75) Inventors: Sushovon S. Roy, Houston, TX (US); Daniel F. Dorffer, Houston, TX (US); Donald L. Crawford, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 713 days.

(21) Appl. No.: 12/447,831

(22) PCT Filed: May 8, 2007

(86) PCT No.: PCT/US2007/068473
§ 371 (c)(1),
(2), (4) Date: Apr. 29, 2009

(87) PCT Pub. No.: WO2008/136834
PCT Pub. Date: Nov. 13, 2008

(65) Prior Publication Data
US 2010/0063738 A1 Mar. 11, 2010

(51) Int. Cl.
G01V 1/28 (2006.01)
G01V 3/18 (2006.01)
E21B 41/10 (2006.01)
E21B 49/08 (2006.01)

(52) U.S. Cl.
USPC ............... 702/12; 702/6; 702/189; 324/324

(58) Field of Classification Search
USPC ........... 702/6, 12, 189; 324/324; 73/152.19, 73/152.23
See application file for complete search history.

(56) References Cited

U.S. PATENT DOCUMENTS

| | | | |
|---|---|---|---|
| 3,706,025 A | 12/1972 | Regat | |
| 4,209,747 A | 6/1980 | Huchital | |
| 4,357,835 A | 11/1982 | Kayama | |
| 4,733,191 A | 3/1988 | Doll | |
| 4,839,644 A | 6/1989 | Safinya et al. | |
| 4,845,433 A | 7/1989 | Kleinberg et al. | |
| 5,189,909 A * | 3/1993 | Oike et al. | 73/152.18 |
| 5,388,455 A | 2/1995 | Hamby et al. | |
| 5,432,446 A | 7/1995 | MacInnis et al. | |
| 5,469,746 A | 11/1995 | Fukunaga et al. | |
| 5,900,733 A * | 5/1999 | Wu et al. | 324/338 |
| 6,085,599 A | 7/2000 | Feller | |
| 6,291,995 B1 | 9/2001 | Speier et al. | |
| 6,384,605 B1 * | 5/2002 | Li | 324/338 |
| 6,489,772 B1 | 12/2002 | Holladay et al. | |
| 6,603,312 B2 | 8/2003 | Sinclair | |
| 6,703,819 B2 | 3/2004 | Gascoyne et al. | |
| 6,734,675 B2 | 5/2004 | Fanini et al. | |
| 6,825,657 B2 * | 11/2004 | Kleinberg et al. | 324/303 |
| 6,938,469 B2 | 9/2005 | Ganesan | |
| 7,024,920 B2 | 4/2006 | Discenzo | |
| 7,457,707 B2 * | 11/2008 | Davydychev et al. | 702/7 |
| 2002/0140425 A1 * | 10/2002 | Prammer et al. | 324/303 |
| 2007/0050145 A1 | 3/2007 | Zhan et al. | |
| 2008/0272931 A1 * | 11/2008 | Auzerais et al. | 340/854.7 |

* cited by examiner

Primary Examiner — Alexander H Taningco
Assistant Examiner — L. Anderson
(74) Attorney, Agent, or Firm — Conley Rose, P.C.

(57) ABSTRACT

An apparatus and method for measuring the conductivity of borehole fluid. Based on the fluid conductivity, the fluid type may also be identified. The apparatus and method can be useful in differentiating between native water and injected water in oil recovery operations. The apparatus and method presented can also be used to calibrate testing and production equipment allowing for more reliable and accurate measurements. The apparatus and method presented can further be used to better characterize water to oil ratio in reservoirs.

26 Claims, 4 Drawing Sheets

FLUID CONDUCTIVITY MEASUREMENT TOOL AND METHODS

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

In oil and gas well drilling operations it may be useful to determine the types of fluid being produced downhole from a formation, such as hydrocarbons in the form of natural gas or oil, and water. Fluids such as water are a common byproduct of petroleum production and can cause difficulties such as reduced hydrocarbon production and increased water disposal costs. Determination and detection of water production may allow the well operator to take appropriate remedial actions can enhance the economic life of individual wells and the petroleum reservoir as a whole.

The fluid being produced may be made up of more than one type of fluid the overall fluid composition may be described in terms of holdup. Holdup is the fraction of a particular fluid present in an interval of pipe or borehole. In addition to composition, the fluid being produced may also be described in terms of flow rate. In multiphase flow, for example, each fluid may move at a different speed due to several factors. The holdup of a particular fluid is not the same as the proportion of the total flow rate due to that fluid, also known as its cut. To determine in-situ flow rates, it is necessary to measure the holdup and velocity of each fluid, the sum of the holdups of the fluids present being unity.

To determine the fluids being produced and the percentage make-up of those fluids in a given volume, a production log operation may be performed using a fluid identification tool like hydro or density sensor to measure the hold of each fluid at a particular depth. For water, the holdup can often be derived from measurements of fluid capacitance and density of the production fluid. Devices that measure capacitance however are less accurate in fluids with high (more than 40%) water cuts because of the nonlinear nature of the tool response above 40% water cut. Devices that measure density are likewise sensitive to increased water salinity which increases conductivity. Density devices also begin to lose resolution in heavy oil, where the density of oil approaches that of water. Recent microwave, radio frequency, and infrared devices used to determine water holdup also experience decreased accuracy in high water content environments. Most microwave probes are also affected by changes in water salinity and oil density.

BRIEF DESCRIPTION OF THE DRAWINGS

For a more detailed description of the embodiments, reference will now be made to the following accompanying drawings.

DETAILED DESCRIPTION OF THE EMBODIMENTS

Figure 1:
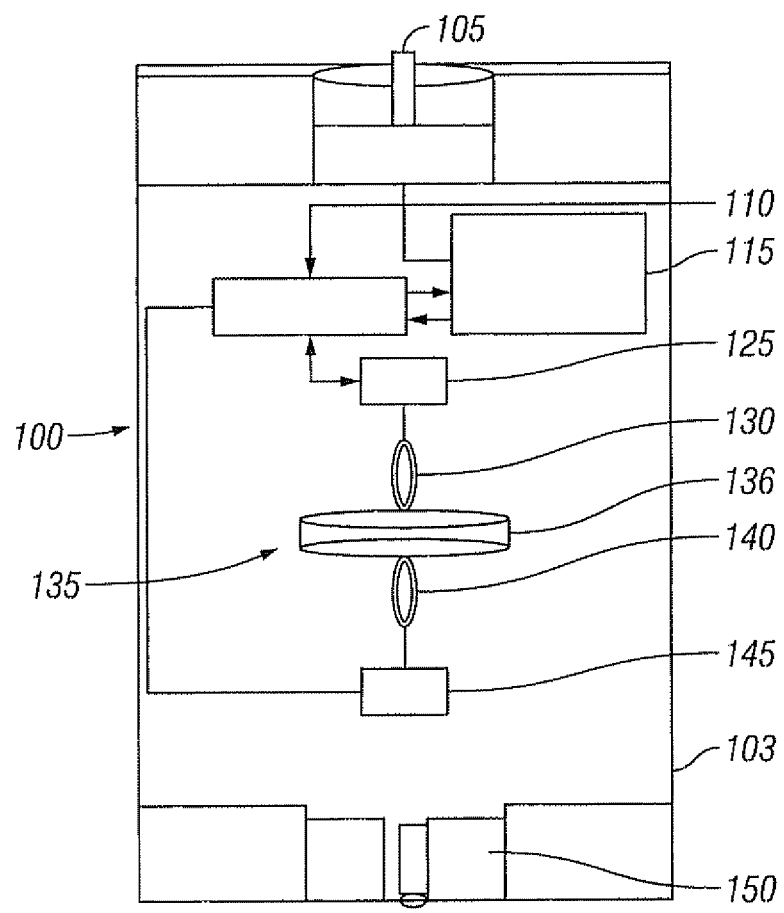
FIG. 1 illustrates a schematic view of an embodiment of a conductivity tool that can be employed alone or in conjunction with other tools downhole.

In the drawings and description that follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results. Any use of any form of the terms "connect", "engage", "couple", "attach", or any other term describing an interaction between elements is not meant to limit the interaction to direct interaction between the elements and may also include indirect interaction between the elements described. The various characteristics mentioned above, as well as other features and characteristics described in more detail below, will be readily apparent to those skilled in the art upon reading the following detailed description of the embodiments, and by referring to the accompanying drawing.

While specific embodiments have been shown and described, modifications can be made by one skilled in the art without departing from the spirit or teaching of this invention. The embodiments as described are exemplary only and are not limiting Many variations and modifications are possible and are within the scope of the invention. Accordingly, the scope of protection is not limited to the embodiments described, but is only limited by the claims that follow, the scope of which shall include all equivalents of the subject matter of the claims.

The apparatus and methods for measurement of conductivity described herein can be used in an open, uncased borehole or cased borehole in oil, gas, and/or water wells. Additionally, water conductivity measurements can be measured continuously or periodically. The apparatus and methods can be used with various conveyance configurations, including wireline, electrical line, pipeline, tubing, coiled tubing, or any similar means, installed permanently downhole, deployed as a separate tool, incorporated in a string of tools, or integrated into a tool as a sensor. The apparatus and methods can also be used for tool calibration. The apparatus and methods can be used in a well that is flowing or a well that is shut-in and engaged in stationary or dynamic conditions. The apparatus and methods can also be used to identify fluid being produced at every level of production.

FIG. 1 illustrates an embodiment of the conductivity tool 100 that can measure the conductivity of borehole fluid. The conductivity of the borehole fluid may optionally then be used to identify the fluid type. The conductivity tool 100 includes a housing 103 including a tool top connection 105 and a tool bottom connection 150 that allows for conveyance of the conductivity tool 100 downhole alone or in connection with a string of tools, pipe, or tubing. Power can be supplied to the tool 100 by either an electrical line extending from the surface or through a self-contained battery located downhole. As shown, the conductivity tool 100 includes a power supply and control 115 that controls a signal processing circuit 110. The signal processing circuit 110 may be an oscillator that generates an electric signal. In addition to being an oscillator, the signal processing circuit 110 may also be a receiver signal processing circuit as described in further detail below. When activated by the power supply and control 115, the signal processing circuit 110 modulates an electric current into a signal and transmits the signal to a transmitter driver circuit 125.

The transmitter driver circuit 125 in turn drives a means for transmitting electromagnetic waves such as transmitter coil 130, which transmits electromagnetic radiation at a selected power and frequency based on the signal sent to the transmitter driver circuit 125. The selected frequency may be correlated to the frequency generated by a fluid of known conductivity, such as water.

FIG. 1 illustrates that the tool 100 also includes a borehole fluid contact 136 configured as a slot where the borehole fluid can enter the conductivity tool 100 and receive electromagnetic radiation from the transmitter coil 130. The borehole fluid 135 can be wholly contained in the conductivity tool 100, partially contained in the conductivity tool 100, or contacted with the conductivity tool 100 in a variety of contact formations. Regardless, the borehole fluid contact 136 allows the transmitted electromagnetic radiation to pass through the borehole fluid 135.

The transmitter coil 130 creates electromagnetic radiation that includes a primary magnetic field, which induces electrical current loops within the borehole fluid 135 at the borehole fluid contact 136, creating a secondary magnetic field in the borehole fluid 135. The currents induced in the borehole fluid are related to both the induced electrical field at each particular point and the conductivity of the borehole fluid 135. Both the primary magnetic field produced by the transmitter coil 130, and the secondary magnetic field, produced by the borehole fluid 135, induce a corresponding electric current in the receiver coil 140, creating a received signal that is a function of the borehole fluid conductivity. Thus, the borehole fluid 135 acts as a receiver with regards to the transmitter coil 130 and as a transmitter with regards to the receiver coil 140.

In this and other embodiments the transmitter coil 130, borehole fluid contact 136, and receiver coil 140 can be arranged in a variety of configurations. Single or multiple transmitter coils 130 and receiver coils 140 can be employed with single or multiple borehole contacts 136. FIG. 1 illustrates the borehole fluid contact 136 as being a slot in the tool housing 103. However, as previously mentioned, the borehole fluid contact may be in any suitable form such that the transmitter coil 130 and the receiver coil 140 are in electromagnetic communication through the borehole fluid. This includes electromagnetic communication through borehole fluid in the housing 103 as well as outside the housing 103 but within the borehole.

The induced electric signal in the receiver coil 140 travels to a receiver electronic circuit 145 capable of processing the received electric signal and then travels to and is amplified by the signal processing circuit 110. The induced signal is then compared to the transmitter signal through a phase sensitive detector in the signal processing circuit 110 and undesired signals are cancelled out. Further modification of the signal, such as required amplification of a known gain may also be performed.

The induced electric signal in the receiver coil 140 may be sent up hole in the form of voltage or current. Or, the signal may be stored in the conductivity tool 100 with a time mark, for example during slick line operations. In the case of electric line operations, e.g., Surface Read Out, the signal can also be multiplexed along with the other sensor signals used in a production logging. Telemetry is used for the multiplexing and a transmitter circuit is used for driving the electric line. In case of memory logging, which is normally done using a slick line or coil tubing, the tool 100 electronics may be powered using a battery and the output data may also be stored inside the tool memory along with the event time. When the tool 100 is retrieved after the survey, the time based data may be converted to depth based using the depth to time converter recorded at the surface. The depth based log may be produced similar to electric line logging.

Comparison of the conductivity of the borehole fluid with fluids of known conductivity may then be performed to determine the bore hole fluid type. The tool 100 is also calibrated with different solutions of known conductivity before being deployed downhole such that any measurement offset will be corrected. For an example, the calibration can be done once a year in the factory using three different NaCl (common salt) solutions. The actual conductivity of the NaCl solution is measured using a precision conductivity measuring devise available in the market and then the apparatus output is plotted with respect to these conductivities. For oil field applications, the following example ranges of conductivity can be used for calibration with the apparatus response being linear. 0.5 to 1 Siemens per meter—Low conductivity range; 5 to 10 Siemens per meter—Medium conductivity range, and 20 to 40 Siemens per meter—High conductivity range. The gain and offset of the calibration is used to convert the apparatus output to conductivity.

The conductivity tool 100 limits the conductivity measurement to measurement of conductivity of the borehole fluid and not the casing, if applicable, or formation. To do so, the conductivity tool 100 uses a set of tuned coils for transmitter and receiver having specific size and inductance, operating frequency, operating power. The spacing of the transmitter coil 103 and the receiver coil 140 is also selected to limit the distance the electromagnetic radiation is transmitted. For example, the spacing of between the transmitter coil 130 and the receiver coil 140 may be set at an appropriate distance to effect measurement of the conductivity of the fluid in the borehole. The spacing may be less than 1 inch to ensure that the conductivity measured comes from the fluid inside the borehole, and not the casing or the formation. Other spacing distances may also be used, however. Also, higher frequencies may help to ensure a smaller depth of investigation. For example, a frequency approximately greater than 20 kHz and/or at least 100 kHz may be used.

In addition to measuring the conductivity of the fluids in the borehole to determine fluid conductivity and/or type, the conductivity tool 100 may also be used in the measurement of the salinity of any water in the borehole. Fluids of differing salinity have different conductivity, i.e., salt water has a higher salinity than fresh water and thus has a higher conductivity. Using this principle, the present apparatus and methods can also be used to differentiate water types of differing salinity. For example, the conductivity tool 100 may be used to differentiate injected water from native water or indicate when water has entered the borehole, thus increasing the accuracy in correcting any borehole effect that may alter measurements made by other downhole tools. The present apparatus and methods can also be used to differentiate between fresh water and salt water.

Measuring borehole fluid conductivity can also be used in oil recovery methods employing water injection into the reservoir. Injected water will be of a different salinity than water produced naturally from the formation into the borehole. Thus, even though a producing well is producing native water of a certain salinity, injected water from a nearby injection well may migrate from the injection well and be produced through the producing well. Changes in conductivity measurements would indicate if injected water from a nearby injection well has entered the borehole.

Once the conductivity measurements have been used to identify the borehole fluids, they can also be used to correct the borehole effect on other sensors. The borehole effect is any anomaly in measurement that is induced by measuring the borehole fluid itself. The conductivity of the borehole fluid as determined by the conductivity tool 100 can be used to correct measurements of saturation of oil, native water, and fresh water in the formation. This would allow for correction in direct measurement to help calibrate other tools. For example, the measured borehole fluid conductivity could be used to correct the measurement taken with a pulse neutron tool. These conductivity measurements could also be used in order to better predict reservoir characteristics.

The conductivity tool 100 can also be used in conjunction with different downhole tools or sensors. For example, the conductivity tool 100 may be used with other downhole tools or sensors for measurement of water holdup for a production logging application, measurement of formation fluid salinity in cased and open hole logging such as testing the formation with a downhole formation tester, measurement of borehole fluid conductivity for a measurement-while-drilling tool, and measurement of water production in an open hole and/or cased hole sampling tool.

Figure 2:
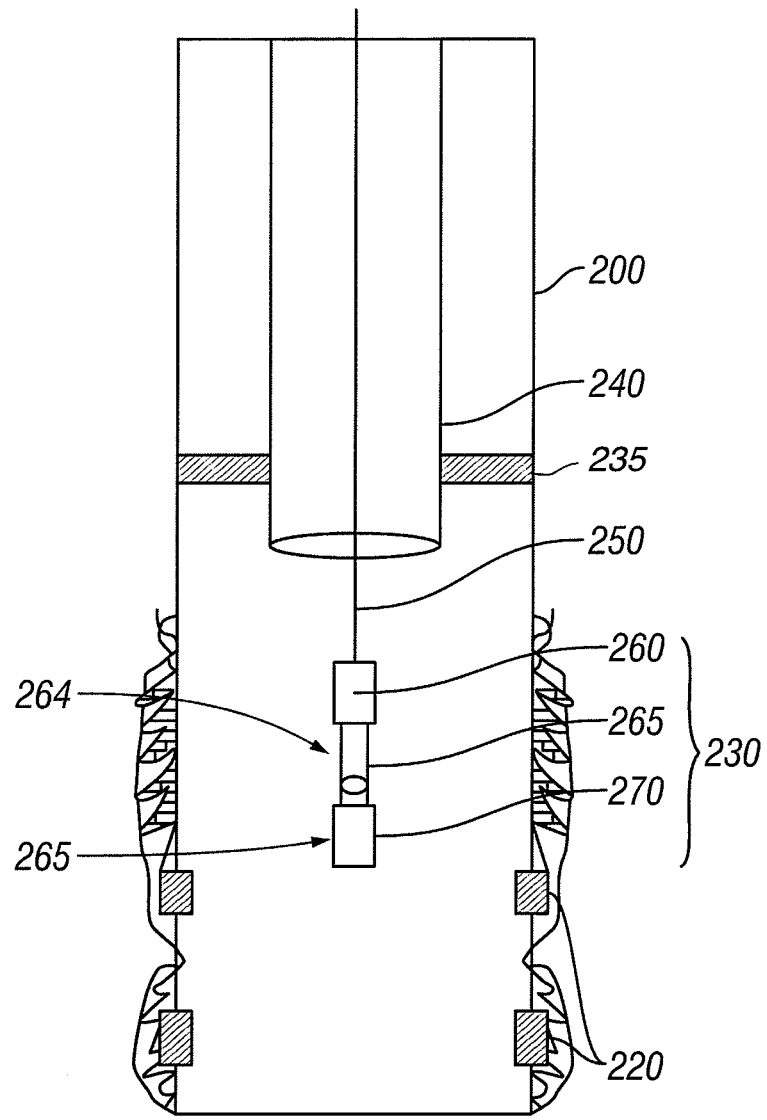
FIG. 2 illustrates a schematic view of an embodiment of the conductivity tool that may be used in measurement of water cut in conjunction with production logging.

FIG. 2 illustrates an embodiment of a conductivity tool 265 used in measurement of water holdup in conjunction with production logging. The conductivity tool 265 is configured as discussed in the embodiment of FIG. 1, with the conductivity tool 265 being connected and working in conjunction with other production tools instead of standing alone. As illustrated, a production tubing 240 is installed in a borehole with casing 200. A packer 235 isolates the annulus between the tubing 240 and the casing 200 that is above the packer 235 from the area below the packer 235. Below the packer 235, the casing 200 is perforated with perforations 220 to allow fluid from the formation to flow into the borehole and be produced by flowing up the tubing 240.

A tool string 230 is conveyed through the tubing 240 by connection to a wireline or slick line 250. The tool string 230 may also be conveyed by any other suitable means such as coiled tubing. The conductivity tool 265 is connected to the production logging tool 260 by its tool top connector 264 and to another production logging tool 270 by its bottom tool connector 265. In an embodiment, the conductivity tool 265 can be used in this manner as a water holdup tool or water salinity tool in conjunction with the other production logging tools, 260, 270 during a production log run.

Figure 3:
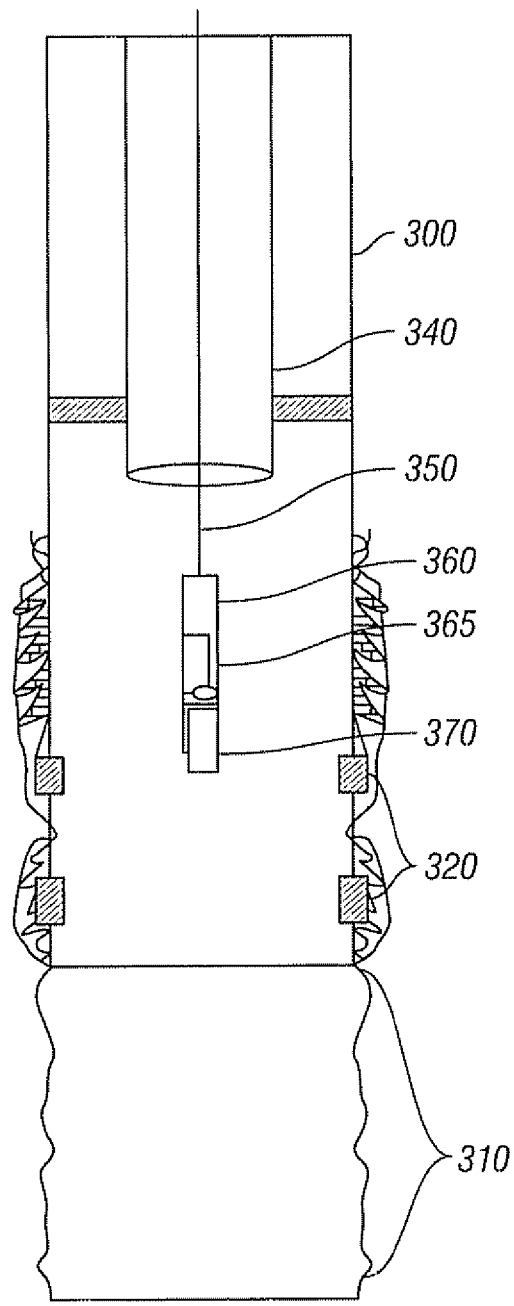
FIG. 3 illustrates a schematic view of an embodiment of the conductivity tool that may be used inside a borehole fluid sample tool.

FIG. 3 illustrates an embodiment of the conductivity used inside a borehole fluid sampling tool 360 in a well 300. A portion of the well 300 may be cased and include perforations 320, and a portion of the well may be open hole 310. The borehole fluid sample tool 360 is conveyed through well tubing 340 by connection to a wireline or slick line 350 or any suitable conveyance means. A conductivity tool 365 is configured as discussed in the embodiment of FIG. 1 with the conductivity tool 365 being integrated into the borehole fluid sample tool 360. The tool 365 may alternatively act as a sensor embodied in the borehole fluid sample tool 360 instead of standing alone, In an embodiment, the conductivity tool 365 uses a sample chamber 370 of the borehole fluid sample tool 360 as a fluid contact to measure the conductivity of the borehole fluid sampled.

Figure 4:
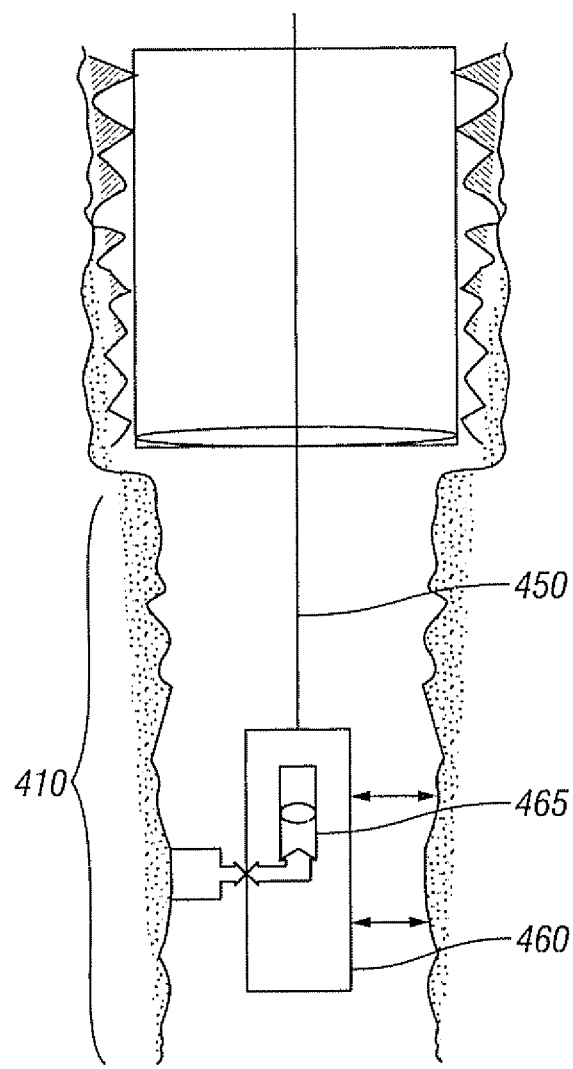
FIG. 4 illustrates a schematic of an embodiment of the conductivity tool that may be used inside a formation tester tool.

FIG. 4 illustrates an embodiment used inside a formation tester tool 460 in an open hole 410. The formation tester tool 460 is conveyed by connection to a wireline, slick line 450, or any other suitable means. A conductivity tool 465 is configured as discussed in the embodiment of FIG. 1 with the conductivity tool 465 being integrated into the formation tester tool 460 or acting as a sensor embodied in formation tester tool 460 instead of standing alone. In an embodiment, the conductivity tool 465 can be used along with the formation tester tool 460 to measure the produced water salinity while sampling borehole fluid or formation fluid.

While specific embodiments have been shown and described, modifications can be made by one skilled in the art without departing from the spirit or teaching of this invention. The embodiments as described are exemplary only and are not limiting. Many variations and modifications are possible and are within the scope of the invention. Accordingly, the scope of protection is not limited to the embodiments described, but is only limited by the claims that follow, the scope of which shall include all equivalents of the subject matter of the claims.

What is claimed is:

1. A fluid conductivity tool for measuring the conductivity of a borehole fluid located in a borehole extending through a formation, the tool comprising:
   a signal processing circuit configured to generate an electric signal;
   a transmitter driver circuit connected to the signal processing circuit and configured to drive a transmitter coil to produce electromagnetic radiation;
   a fluid contact with access to the borehole fluid such that borehole fluid can enter the tool and electromagnetic radiation from the transmitter coil is passable through the borehole fluid in the fluid contact;
   a receiver coil configured to receive the electromagnetic radiation after passing through the borehole fluid in the fluid contact and converting the electromagnetic radiation into a received electric signal;
   a receiver electronic circuit configured to process the received electric signal; and
   wherein the signal processing circuit configured to receive data from the receiver electronic circuit and compare the electric signal to the received electric signal to determine the conductivity of the borehole fluid.

2. The tool of claim 1, wherein the borehole is a cased borehole.

3. The tool of claim 1, wherein the transmitter coil and the receiver coil are placed less than 1 inch apart.

4. The tool of claim 1, wherein the conductivity of the formation does not affect the measurement of the conductivity of the borehole fluid.

5. The tool of claim 1, further comprising a processor located at the surface that can receive data relating to the transmitted and received signals transmitted from downhole to the surface.

6. The tool of claim 1, wherein the transmitter coil, fluid contact, and receiver coil are included in a tool string downhole.

7. The tool of claim 1, wherein the tool is integrated into a measurement-while-drilling tool.

8. The tool of claim 1, wherein the tool is configured to provide data relating to the conductivity of the borehole fluid to another downhole tool.

9. The tool of claim 8, wherein the other downhole tool is a tool selected from at least one of the group consisting of a measurement-while-drilling tool, a downhole formation tester, a production logging tool, a borehole fluid sample tool, and a pulse neutron tool.

10. A method for measuring the conductivity of a borehole fluid located in a borehole extending through a formation, the method comprising:
    disposing a measurement tool in the borehole;
    generating a transmitted electric signal;
    converting the transmitted electric signal into electromagnetic radiation;
    allowing borehole fluid to enter the tool at a fluid contact;
    transmitting the electromagnetic radiation through the borehole fluid in the fluid contact;
    receiving the electromagnetic radiation after passing through the borehole fluid in the fluid contact;
    converting the received electromagnetic radiation into a received electric signal; and
    comparing the transmitted electric signal and the received electric signal to determine the conductivity of the borehole fluid.

11. The method of claim 10, further comprising identifying the borehole fluid based on the conductivity of the borehole fluid.

12. The method of claim 10, wherein the borehole is a cased borehole.

13. The method of claim 10, further comprising transmitting the electromagnetic radiation using a transmitter coil and receiving the electromagnetic radiation using a receiver coil, and wherein the transmitter coil and receiver coil are placed less than 1 inch apart.

14. The method of claim 10, wherein the conductivity of the formation does not affect the measured conductivity of the borehole fluid.

15. The method of claim 10, further comprising comparing the transmitted electric signal and the received electric signal downhole.

16. The method of claim 10, further comprising transmitting data relating to the transmitted electric signal and the received electric signal to the surface for determining the conductivity of the borehole fluid.

17. The method of claim 10 further comprising transmitting and receiving the electromagnetic radiation using a component in a tool string comprising other downhole tools.

18. The method of claim 10, further comprising using the computed conductivity of the borehole fluid to adjust the measurement of a downhole tool.

19. The method of claim 10 further comprising determining the conductivity of borehole fluid obtained using a formation tester.

20. The method of claim 10 further comprising transmitting data relating to the conductivity of the borehole fluid to a pulse neutron tool.

21. A system for providing a measurement of fluid conductivity of a borehole fluid, comprising:
    a tool comprising:
        a signal generator configured to generate a transmitted signal;
        a fluid contact configured to be fluidly coupled to the borehole fluid;
        a wave transmitter configured to transmit a plurality of electromagnetic waves through the borehole fluid in the fluid contact based on the transmitted signal;
        a wave receiver configured to receive the plurality of electromagnetic waves from the borehole fluid in the fluid contact and configured to convert the received electromagnetic waves into a received signal; and
        a processor configured to compare the transmitted signal with the received signal to determine the conductivity of the borehole fluid.

22. The system of claim 21, wherein the processor is configured to identify the borehole fluid based on the computed borehole fluid conductivity.

23. The system of claim 21, wherein the borehole fluid is contained and surrounded by casing during measurement.

24. The system of claim 21, wherein the fluid contact comprises a sample chamber.

25. The tool of claim 1, wherein the fluid contact comprises a sample chamber.

26. The method of claim 10, wherein the fluid contact comprises a sample chamber.

* * * * *